(12) United States Patent
Zeroni et al.

(10) Patent No.: US 9,770,259 B2
(45) Date of Patent: Sep. 26, 2017

(54) CATHETER WITH HELICAL DRIVE SHAFT AND METHODS OF MANUFACTURE

(71) Applicant: Covidien LP, Mansfield, MA (US)

(72) Inventors: Jenny Zeroni, Plymouth, MN (US); Cory David Sills, Plymouth, MN (US); Victoria Schuman, Minneapolis, MN (US); Marc D. Knutson, Robers, MN (US); Bryan Matthew Ladd, St. Louis Park, MN (US); Benjamin Robert Fruland, Blaine, MN (US); Lucas Schneider, Champlin, MN (US); Alexander J. Rice, Hutchinson, MN (US)

(73) Assignee: Covidien LP, Mansfield, MA (US)

( * ) Notice: Subject to any disclaimer, the term of this patent is extended or adjusted under 35 U.S.C. 154(b) by 52 days.

(21) Appl. No.: 14/642,811

(22) Filed: Mar. 10, 2015

(65) Prior Publication Data

US 2015/0238223 A1 Aug. 27, 2015

Related U.S. Application Data

(62) Division of application No. 13/599,526, filed on Aug. 30, 2012, now Pat. No. 8,992,717.

(Continued)

(51) Int. Cl.

| | |
|---|---|
| *A61B 17/3207* | (2006.01) |
| *B29C 53/14* | (2006.01) |
| *A61M 25/00* | (2006.01) |
| *B29C 65/18* | (2006.01) |
| *B29C 65/00* | (2006.01) |

(Continued)

(52) U.S. Cl.
CPC ........... *A61B 17/320783* (2013.01); *A61B 17/320758* (2013.01); *A61M 25/0009* (2013.01); *B29C 53/14* (2013.01); *B29C 65/18* (2013.01); *B29C 66/532* (2013.01); *A61B 2017/00526* (2013.01); *B29K 2077/00* (2013.01);

(Continued)

(58) Field of Classification Search
None
See application file for complete search history.

(56) References Cited

U.S. PATENT DOCUMENTS

| | | |
|---|---|---|
| 1,481,078 A | 1/1924 | Albertson |
| 2,178,790 A | 11/1939 | Henry |

(Continued)

FOREIGN PATENT DOCUMENTS

| | | |
|---|---|---|
| CA | 2000621 | 4/1990 |
| DE | 3732236 C1 | 12/1988 |

(Continued)

OTHER PUBLICATIONS

International Search Report and Written Opinion dated Mar. 12, 2013 for PCT/US2012/053181, 17 pages, Rijswijk, The Netherlands.

(Continued)

*Primary Examiner* — Barbara J Musser

(57) ABSTRACT

Drive shafts having helical blades and methods of making are disclosed. In one method a helical auger blade is formed by twisting or sculpting a heated polymer tube which has been placed over a cylindrical drive shaft. In another method a drive shaft is placed within a helical winding and heat is applied to melt polymer which has been coated over one or both of the drive shaft and helical winding.

20 Claims, 10 Drawing Sheets

Related U.S. Application Data

(60) Provisional application No. 61/530,299, filed on Sep. 1, 2011.

(51) Int. Cl.
    *B29L 31/00*         (2006.01)
    *A61B 17/00*        (2006.01)
    *B29K 77/00*        (2006.01)
    *B29K 705/00*       (2006.01)

(52) U.S. Cl.
    CPC ... *B29K 2705/00* (2013.01); *B29L 2031/7542* (2013.01); *Y10T 156/1043* (2015.01)

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,108,525 A | 4/1992 | Gharibadeh |

(56) References Cited

U.S. PATENT DOCUMENTS

| | | |
|---|---|---|
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |

(56) References Cited

U.S. PATENT DOCUMENTS

| | | |
|---|---|---|
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,906,036 A | 5/1999 | Pagan |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,267,592 B1 | 7/2001 | Mays |
| 6,277,138 B1 | 8/2001 | Levinson et al. |

(56) References Cited

U.S. PATENT DOCUMENTS

| | | |
|---|---|---|
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antoniades et al. |
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 * | 5/2003 | Clement ........ A61B 17/320758 604/22 |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson et al. |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0116039 A1 | 8/2002 | Walker et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2004/0236346 A1 * | 11/2004 | Parker ............... A61M 25/0045 606/108 |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |

(56) References Cited

U.S. PATENT DOCUMENTS

| | | |
|---|---|---|
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik et al. |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0275966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |
| 2012/0172905 A1* | 7/2012 | Lee Shee ............ A61B 17/1671 606/180 |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 107 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A1 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0 983 749 A2 | 3/2000 |
| EP | 1 767 159 A1 | 3/2007 |
| EP | 1 875 871 A2 | 1/2008 |
| GB | 2016354 A | 9/1979 |
| GB | 2093353 A | 9/1982 |
| GB | 2 115 829 A | 9/1983 |
| GB | 2210965 A | 6/1989 |
| JP | 64-084523 | 3/1989 |
| JP | 2-206452 A | 8/1990 |
| JP | 02-280765 | 11/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8965817 A1 | 7/1989 |
| WO | 9001406 | 2/1990 |
| WO | WO 92/07500 A2 | 5/1992 |
| WO | WO 9313716 A1 | 7/1993 |
| WO | WO 9313717 A1 | 7/1993 |
| WO | 9316642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | WO 00/30531 A1 | 6/2000 |
| WO | WO 00/54735 A1 | 9/2000 |
| WO | WO 00/62913 A1 | 10/2000 |
| WO | WO 00/63800 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 02085440 A2 | 10/2002 |
| WO | 2006058223 A2 | 6/2006 |
| WO | 2006066012 A2 | 6/2006 |

OTHER PUBLICATIONS

Notice of Reasons for Rejection from Japanese Application No. 2014-528609, Dated Nov. 19, 2014, 9 pages.
Brezinski et al., "Optical Coherence Tomography for Optical Biopsy," Circulation, 93:1206-1213 (1996).
Brezinski et al., "Assessing Atherosclerotic Plaque Morphology: Comparison of Optical Coherence Tomography and High Frequency Intravascular Ultrasound," Heart, 77:397-403 (1997).
Huang et al., "Optical Coherence Tomography," Science, 254:1178-1181 (1991).
Amplatz Coronary Catheters, posted: Feb. 25, 2009, [online], [retrieved on Mar. 29, 2011], retrieved from the Cardiphile MD using Internet website <URL:http://cardiophile.org/2009/02/amplatzcoronary-catheter.html> (3 pages).
Judkins Left Coronary Catheter, posted: Feb. 19, 2009, [online], [retrieved on Mar. 29, 2011], retrieved from the Cardiphile MD using Internet website <URL:http://cardiophile.org/2009/02/judkins-left-coronary-catheter.html> (3 pages).

* cited by examiner

CATHETER WITH HELICAL DRIVE SHAFT AND METHODS OF MANUFACTURE This application is a divisional application of U.S. Ser. No. 13/599,526, filed Aug. 30, 2012 now U.S. Pat. No. 8,992,717, which claims the benefit of U.S. Provisional Patent Application No. 61/530,299, filed Sep. 1, 2011, entitled "Catheter with Helical Drive Shaft and Methods of Manufacture", the contents of which are hereby incorporated by reference herein.

FIELD OF THE INVENTION

The present invention relates to drive shafts for use in tissue removal devices. More particularly, this invention pertains to a catheter having a helical drive shaft with an auger shaped outer surface and methods of manufacturing those drive shafts.

BACKGROUND OF THE INVENTION

Atherosclerosis is a progressive disease of the vascular system whereby atheroma is deposited on the inner walls of blood vessels. Atherosclerosis is a complex, progressive and degenerative condition resulting in the build-up of cholesterol and other obstructive materials, known as plaque, on the walls of the arteries. The accumulation of plaque narrows the interior or lumen of blood vessels, such as arteries, thereby reducing blood flow.

Plaque occurs in several different forms and may be located in many different anatomies throughout the vascular system. Plaque varies in composition, with portions that are hard and brittle, referred to as calcified plaque, and other portions that are fatty or fibrous. Over time atheromatous deposits can become large enough to reduce or occlude blood flow through the vessels, leading to symptoms of low blood flow, such as pain in the legs (on walking or at rest), skin ulcer, angina (at rest or exertional), and other symptoms. To treat this disease and improve or resolve these symptoms it is desirable to restore or improve blood flow through the vessel.

Various means are used to restore or improve blood flow through atheromatous vessels. The atheroma deposits may be displaced by diametrically expanding the vessel by inflating balloons, expanding stents, and other methods. The deposits may be pulverized using lasers and other methods. Atherectomy catheters may also be used to remove atheromatous deposits from the blood vessel.

Many types of atherectomy catheter devices have been proposed, including catheters with rotating burrs, or lasers to photo-dissolve tissue. Other atherectomy catheters have cutting elements that extend through or beyond an opening in the distal end of the catheter to cut tissue or that cut tissue through a side opening or window in the catheter body. Some of these catheters use balloons or other positioning devices to position the cutter adjacent material to be removed.

One catheter design attempts to capture the removed plaque in a collection or storage chamber so that it can be removed from the vessel. In use, the storage or collection location may fill up with excised tissue debris. If the storage or collection location is contained within the catheter body, a cleaning procedure may require the physician to remove the device to empty the collection chamber.

As used in this application the term "distal" refers to a direction away from the operator and the term "proximal" refers to a direction towards the operator. Thus, the handle of the device is located at the "proximal end" and the "distal end" is the end of the device that is inserted first into the vessel. One recent atherectomy catheter, the SILVERHAWK articulated rotating blade atherectomy catheter, (sold by Covidien) has been designed to treat atherosclerotic plaque by excising it from the artery. The SILVERHAWK catheter (features of which are exemplified in U.S. patent application Ser. Nos. 10/027,418; 10/288,559; 10/896,747; and others) uses a rotating blade, a side cutting window through which the blade can be extended, and a hinged nose design which can be controlled to cause the catheter to assume a straight position or an angled position. During the cutting procedure the catheter is in the angled position so the side cutting window and cutting blade can be urged against the vessel wall. The SILVERHAWK catheter is moved distally through the lesion during the cutting procedure. The SILVERHAWK catheter includes a collection chamber located in a distal portion of the catheter nose distal of the cutting window. The cutting blade and cutting window are configured to direct material cut from the vessel wall through the cutting window and into the collection chamber.

In some tissue cutting devices the collection chamber is located proximal of the tissue cutting element. For example, in co-pending U.S. patent application Ser. No. 13/160,044 filed Jun. 14, 2011, the contents of which are incorporated herein by reference in their entirety, an atherectomy catheter having a proximally located collection chamber is disclosed. The catheter includes a side cutting window and a cutting blade configured to extend through the window to cut material from the wall of a vessel at a treatment site as the catheter is pulled proximally through the treatment site. The catheter includes a material collection chamber which is positioned proximally of the cutting window. During use the cutting window is advanced distal to the treatment site, the cutting blade is extended out the window and material is cut from the treatment site by pulling the catheter proximally across the treatment site. In one of the embodiments the drive shaft is provided with auger blades to help transport cut material proximally to the collection chamber.

Although material cutting devices using auger blades to transport cut material, such as the one described above, have been proposed there are design challenges which must be met in order for the devices to function properly in the environment in which they are used. Therefore, there is need for an atherectomy catheter capable of meeting these design challenges.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

DETAILED DESCRIPTION

Apparatus according to the present invention will generally comprise of catheters having catheter bodies adapted for intraluminal introduction to the target body lumen. The body lumen may include arteries or veins in the vascular system, or may be other similar types of body lumens. The dimensions and other physical characteristics of the catheter bodies will vary significantly depending on the body lumen which is to be accessed. In the exemplary case of atherectomy catheters intended for intravascular introduction, the distal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments which are described herein as being configured for use with a guidewire.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of catheters intended for peripheral intra-arterial use, the length is typically in the range from 100 cm to 160 cm, and the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), polyamides, silicone rubbers, natural rubbers, and the like. Optionally, the catheter body may be reinforced with braid, helical wires, coils, axial filaments, or the like, in order to increase rotational strength, column strength, toughness, pushability, kink resistance, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, including both coronary arteries and peripheral arteries, by conventional techniques.

Figure 1:
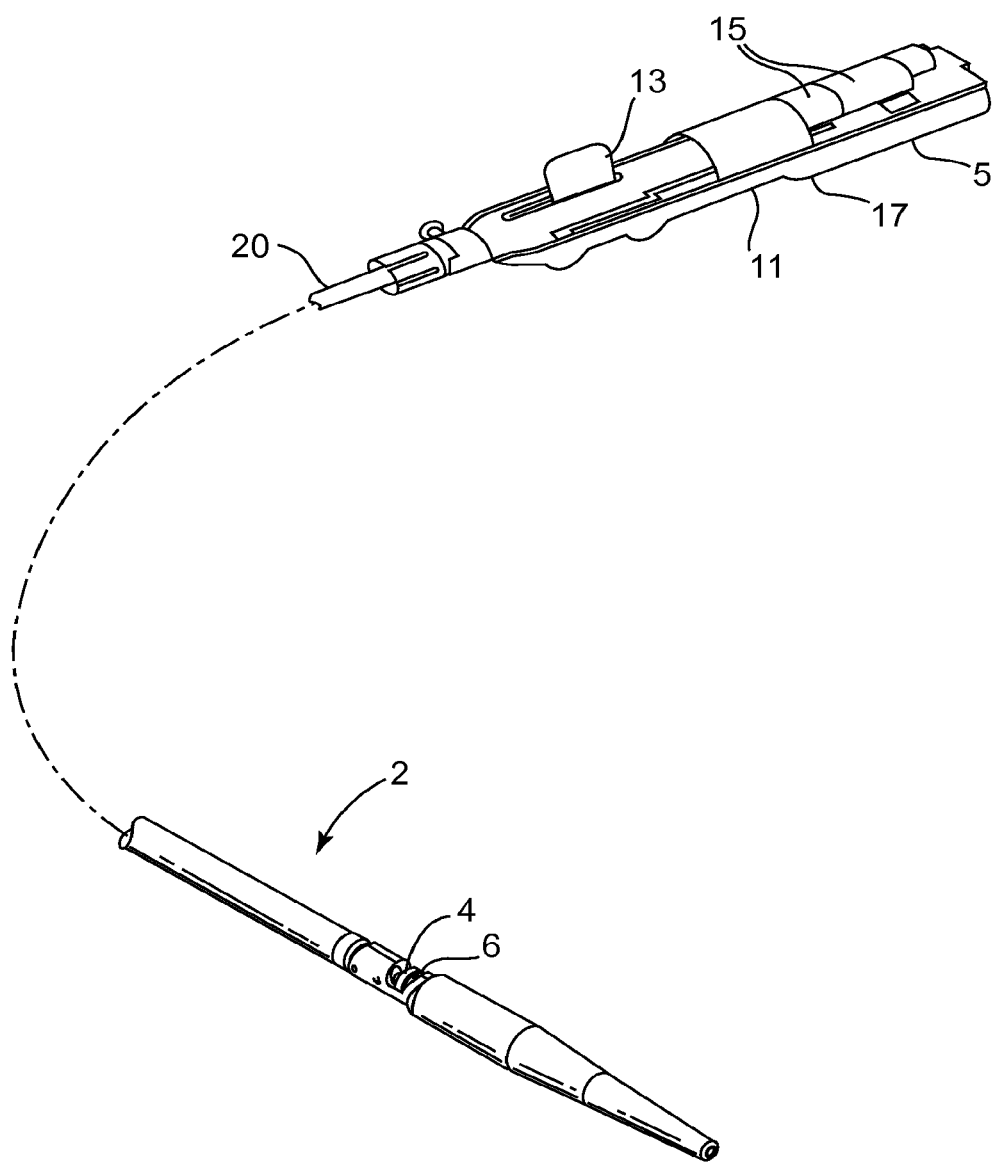
FIG. 1 is a partial isometric view of an atherectomy catheter.

Referring to FIG. 1, an atherectomy catheter 2 is shown. Catheter 2 includes a catheter body connected at its proximal end to a control handle. Located in a lumen of the catheter body is a drive shaft 20 connected at its distal end to a cutting element 4 and at its proximal end to a drive motor located within the handle or cutter driver 5. The drive shaft 20 may be comprised of a high modulus material or composite with flexibility and torquability, e.g. a NiTi tube, stainless steel coil, or other composite layered polymer or metal material. In some embodiments the cutting element 4 is configured to cut tissue that extends through a side opening or cutting window 6 in the catheter body and in other embodiments the cutting element 4 is configured to extend from a distal opening in the catheter body to cut material from the vascular lumen. Cutting elements within the scope of this invention include those which cut tissue or material while the catheter is advanced distally, retracted proximally or maintained stationary.

Catheter 2 is coupled to exemplary cutter driver 5. Cutter driver 5 is comprised of motor 11, power source 15 (for example one or more batteries), microswitch (not shown), housing 17 (upper half of housing is removed as shown), lever 13 and connection assembly (not shown) for connecting shaft 20 to driver motor 11. Cutter driver 5 can act as a handle for the user to manipulate catheter 2. Lever 13, when actuated to close the microswitch, electrically connects power source 15 to motor 11 thereby causing rotation of cutting element 4. The cutting element 4 is rotated about a longitudinal axis LA when the shaft rotates. The cutting element 4 is rotated at about 1 to 160,000 rpm but may be rotated at any other suitable speed depending upon the particular application.

Figure 2:
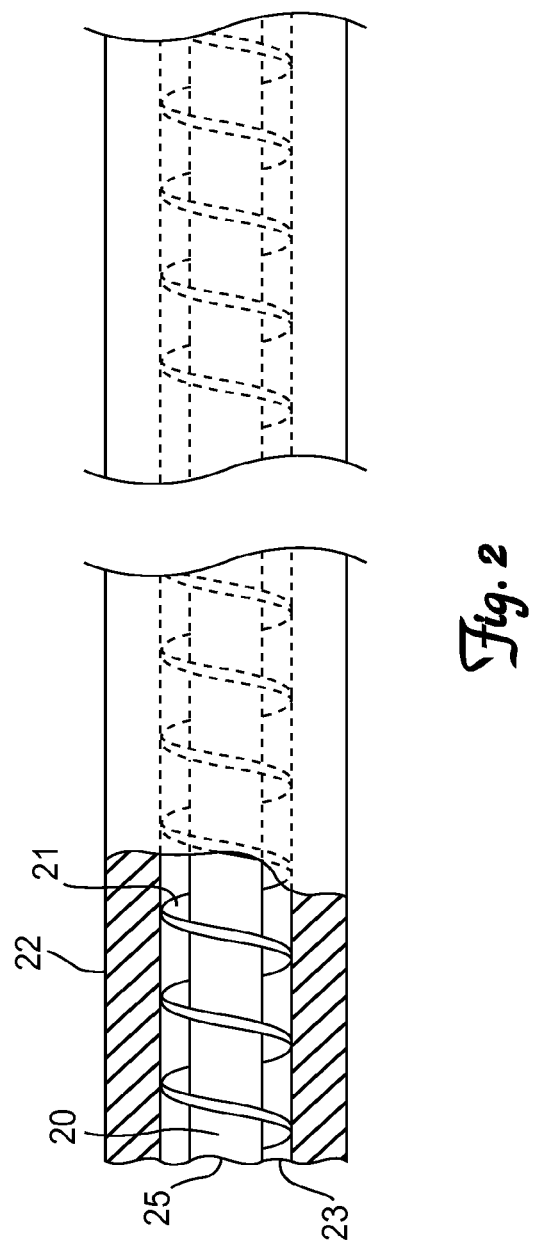
FIG. 2 is a partial cross-sectional view of a portion of the body of the atherectomy catheter of FIG. 1 showing portions of the drive shaft and helical auger blade.

FIG. 2 is a cross-sectional view of a portion of the catheter body 22 showing the drive shaft 20 and helical auger blade 21 which together form helical drive shaft 25 contained within the lumen 23 of the catheter body. As used herein, the term "drive shaft" refers to a generally cylindrical drive shaft which may be solid, hollow, braided, and/or stranded such as drive shaft 20a shown in FIG. 3, or any other composition. The term "helical drive shaft" refers to the combination of a cylindrical drive shaft and a helical winding, as described in more detail hereafter. In the illustrated embodiment, the helical drive shaft 25 both transports removed or cut tissue proximally in the catheter body and drives rotation of the cutting element 4. In other embodiments the helical drive shaft 25 may transport removed or cut tissue proximally within the catheter body 22 but may not drive rotation of a cutting element. FIG. 2 shows the drive shaft 20 proximal of the location where the drive shaft 20 is attached to the cutting element 4. The drive shaft 20 is oriented in this figure such that the proximal and distal ends of the drive shaft 20 (not shown) would lie to the left and right sides of this figure, respectively.

Figure 3:
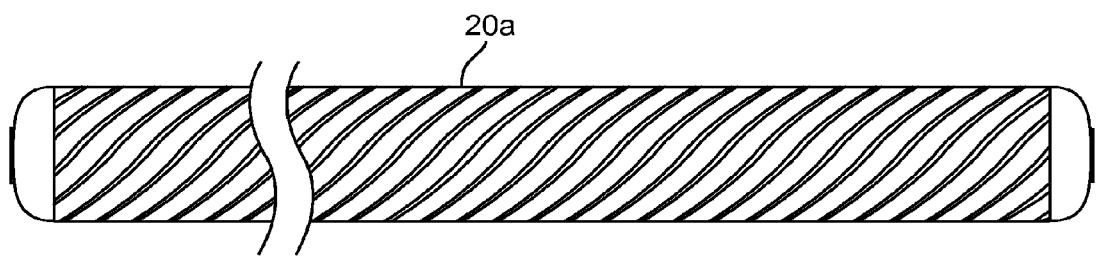
FIG. 3 is a side view of an embodiment of a drive shaft of the present invention.

The drive shaft 20 is generally cylindrical and may comprise a solid tube, a hollow tube, or may be formed from multiple layers of wire wound in alternating right and left hand layers such as drive shaft 20a shown in FIG. 3. The drive shaft with helical auger structure is manufactured to be flexible enough to allow the catheter to navigate tortuous vessel anatomy and strong enough to withstand the stresses encountered by high speed rotation, transmission of torque through the augered driveshaft to the cutter at the distal tip of the device, and transport of calcified material. The helical structure may be a separate element which is attached or affixed in some manner to a substantially cylindrical drive shaft that is composed of multiple counterwound layers as shown in FIG. 3. Alternatively, the drive shaft and helical structure may be formed as a single unitary element incorporating multiple counterwound layers. To withdraw tissue distally, the helical auger must be driven in a direction opposite to its winding direction. This spinning motion tends to cause the helix to unwrap and fail structurally, so the auger and driveshaft must be designed in such a way as to counteract these forces to prevent damage to the auger or to the driveshaft. A counterwound driveshaft enables sufficient torque transmission to meet the design constraints described above, but attachment to the auger is challenged by the conflicting directions of forces experienced by adjacent counterwound layers.

Figure 6:
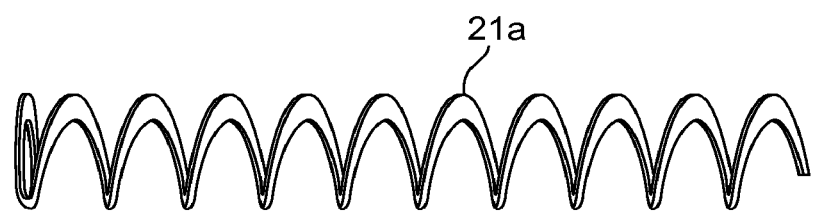
FIG. 6 is a plan view of a helical winding used in the formation of the auger blade in some of the embodiments of the present invention.

Positioned about the drive shaft 20 in the embodiments disclosed herein is a helical winding forming the helical auger blade 21 that is continuous for a least a portion or all of the drive shaft, as desired. In one example, the auger outer diameter may range from about 0.010 inches to about 0.100 inches, and the pitch may range from about 0.010 inches to about 0.25 inches, with the possibility of multiple helices combined to form one auger in a double-helix or multiple-helix configuration. As used herein the terms "helical winding", "auger blade" or "auger blades" are meant to encompass both single and multiple helix designs. The inner diameter of the auger blade 21 is sized to receive the drive shaft. The auger blade 21 or winding may be fixedly attached to the drive shaft 20 along its entire length or at intermittent locations or may be constructed in a floating configuration adjacent, but not attached, to the drive shaft. The auger blade 21 may be wound in a left-handed winding pattern, as depicted in FIGS. 2 and 6, or optionally, a right-handed winding may be used instead. In either case, the helix would be rotated in a direction so as to draw material proximally. The lumen 23 of the catheter body 22 may optionally be attached to a source of suction (not shown) to assist in the transport of the material proximally.

Figure 4:
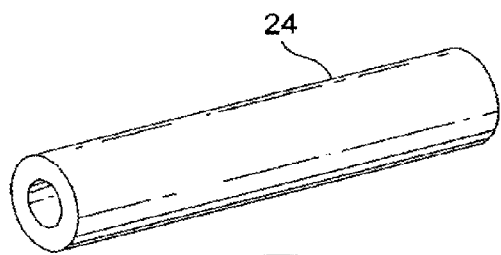
FIG. 4 is a perspective view of a cylindrical layer or tube used in the formation of the auger blade in some of the embodiments of the present invention.
Figure 5:
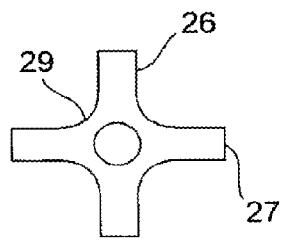
FIG. 5 is a cross-sectional view of a tube having a star shaped cross-section used in the formation of the auger blade in some of the embodiments of the present invention.

Various embodiments and/or methods of associating or attaching a helical winding (auger blades) to a drive shaft to form a helical drive shaft are described herein. In accordance with the present invention the helical drive shaft will have auger blades or fins having a desired pitch, depth or radial length, width or thickness and outer diameter. In some methods the helical winding is formed starting from a generally cylindrical layer of nylon or other polymer, such as tubular member 24 shown in FIG. 4, which is reflowed, ablated, extruded or otherwise formed to receive a drive shaft. In other methods the polymer layer has a star shaped cross-section such as star shaped member 26 as shown in FIG. 5. Star shaped member 26 comprises alternating peaks 27 and valleys 29. Other methods use a metal wire made of copper, stainless steel, NiTi, a cobalt alloy, or other metal alloy having a rectangular cross-section with desired dimensions which is formed into the shape of a helical winding such as auger blade 21a shown in FIG. 6. A portion of drive shaft 20 having a layer of polymer having a depth D1, such as tubular member 24, is shown in cross-section in FIG. 7. The present invention includes all of the methods described herein for forming or making helical drive shafts, the helical drive shafts which are produced by such methods and the catheters that include these helical drive shafts.

Figure 7:
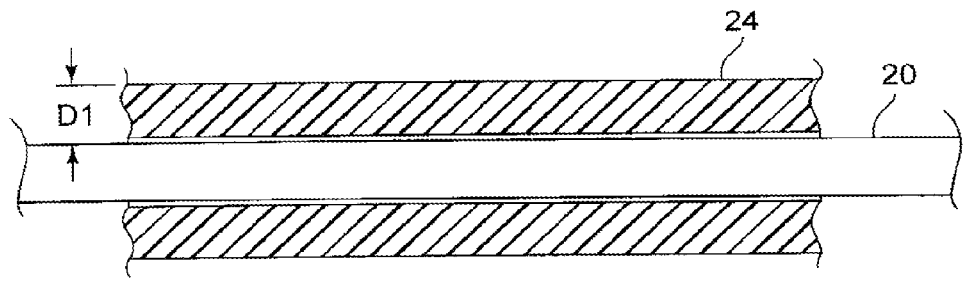
FIG. 7 is a partial cross-sectional view of a portion of the drive shaft of FIG. 3 received within the tube of FIG. 4.
Figure 8:
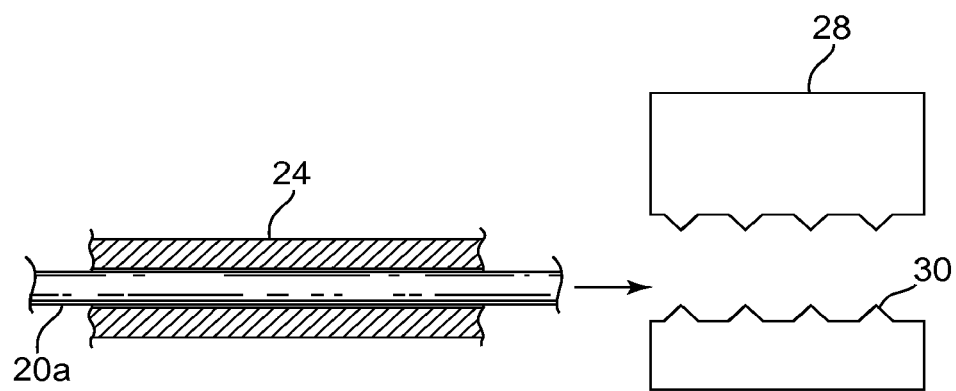
FIG. 8 is a schematic view in partial cross-section of a coated drive shaft being fed through a die.

In a first method, a drive shaft such as drive shaft 20a shown in FIG. 3 has been coated with a layer of polymer 24 (such as seen in FIG. 7) to a depth which is thicker that the desired dimension of the helical winding or auger blade. The polymer layer 24 may be reflowed, extruded, or in some other manner adhered to the outer surface of the drive shaft 20a, such as by the use of adhesives. The coated drive shaft is then screwed through a die 28 with internal threads 30 such as shown in FIG. 8 to form a helical drive shaft such as helical drive shaft 25 shown in FIG. 2. The threads 30 are configured to form the desired pitch and width of the auger blade 21. The die 28 may be spun to allow convenient auger blade formation on the drive shaft 20a without needing to rotate the drive shaft stock and finished parts. In an alternative embodiment a drive shaft itself rotates through a fixed die. In this embodiment, due to the threads 30, the part can be spun and will be self feeding. During this process the die 28 can be heated to promote movement of the material through the die.

Figure 9:
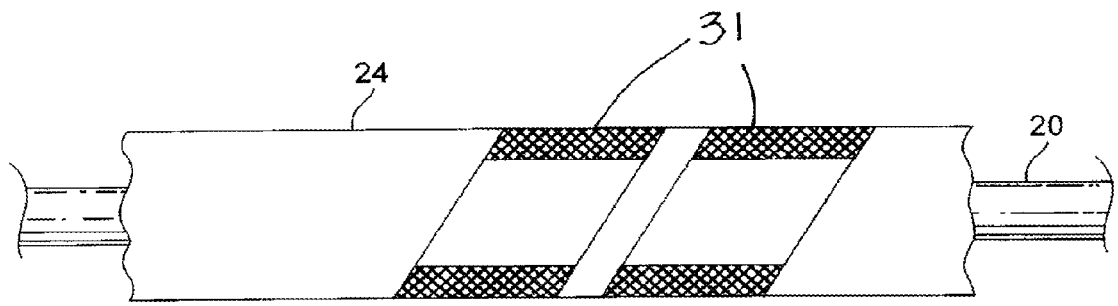
FIG. 9 is a partial cross-sectional view of a coated drive shaft during a cutting process used in formation of an auger blade.

FIG. 9 illustrates another method of associating the auger blade with the drive shaft to form a helical drive shaft. In this method the drive shaft 20 is coated with a polymer layer 24 similar to the one shown in FIG. 7. Next, a helical groove 31 (shown cross-hatched in FIG. 9) is cut into the polymer layer 24 to a desired depth, pitch, thickness and shape using laser ablation or mechanical means such as a lathe to form the auger blade.

Figure 10:
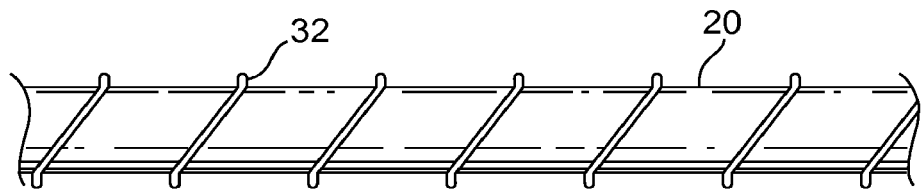
FIG. 10 is a schematic view showing the application of glass to the surface of a drive shaft.
Figure 11:
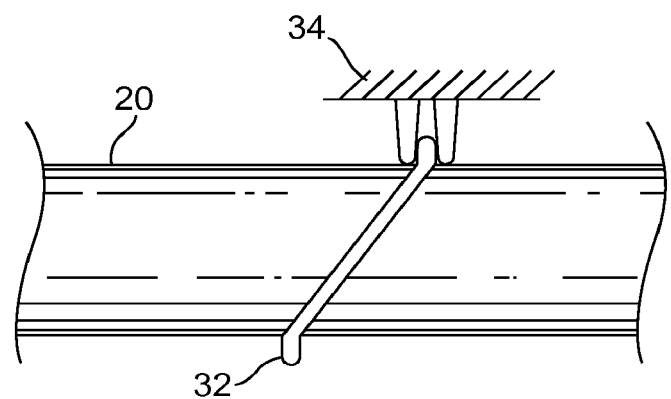
FIG. 11 shows the drive shaft and applied glass of FIG. 10 being shaped in a die.

In another method, a glass helix is formed on the surface of the drive shaft 20 by dripping melted Si (glass) 32 over the surface of the drive shaft in a helical pattern in the manner shown in FIG. 10. Next, as shown in FIG. 11, the drive shaft 20 is placed into a die 34 which is configured to shape the glass 32 into the desired helical shape. In this process the glass provides a base. A polymer coating is then applied over the cylindrical portion and glass base by dip coating, spray coating, vapor deposition, or similar process. The polymer coating forms an outer layer with a raised helical winding in the areas overlying the glass 32. This method results in the production of a helical drive shaft comprising a drive shaft, a layer of glass in a helical pattern adjacent the outer surface of the drive shaft, and an outer coating of polymer.

Figure 12:
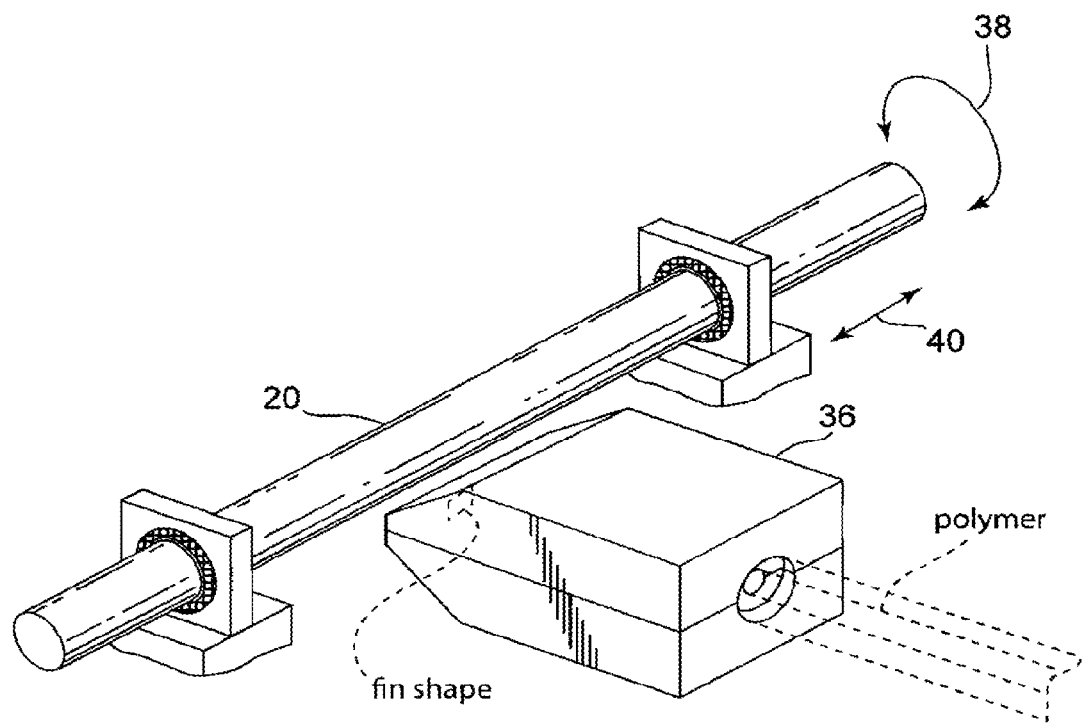
FIGS. 12 and 13 are schematic representations of a process of attaching a helical winding to a drive shaft using an enhanced extrusion process.
Figure 13:
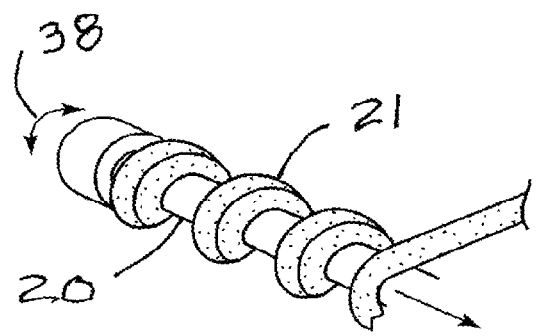

FIGS. 12 and 13 (Note: be sure FIG. 13 contains the appropriate reference numerals) show a process of bonding or attaching a helical winding or auger blade 21 to the drive shaft 20 with an enhanced extrusion process. In this process the drive shaft 20 is positioned directly in front of and perpendicular to an extrusion die 36 as shown schematically in FIG. 12. The drive shaft 20 has its two ends mounted on a rotating apparatus that rotates the drive shaft as shown by arrow 38. The rotating apparatus rests on a linear slide that imparts linear motion to the drives shaft 20 in the direction shown by arrow 40. In this embodiment the extrusion die 36 is configured to the desired shape of the fin or blade of the desired helix. A polymer fin is thus extruded through the die and, while it is still pliable, wound onto the surface of the drive shaft as the drive shaft is rotated and moved sideways past the die as best seen in FIG. 13. In one example, the drive shaft 20 comprises one or more layers of helically-wound wires or filars (e.g., at least two layers of alternating right and left hand filar layers). In this example, the extruded polymer fin flows into spaces or gaps between adjacent filars so that the formed extruded auger blade 21 is fixed to the drive shaft by a mechanical lock. In one embodiment, during the process the drive shaft 20 is rotated circumferentially and slid axially to create a helix with the desired pitch. The process may either be performed using a continuous length of spooled drive shaft 20 or alternately may be performed with discrete lengths of drive shaft. To extrude the helix 21 onto discrete lengths of drive shaft 20, the two ends of each drive shaft may be clamped and pulled axially apart to create tension in the drive shaft. The entire drive shaft 20 is then rotated circumferentially and slid axially as described above. Alternatively, if a continuous length of spooled drive shaft is used instead, the same rotation and sliding motion may be accomplished using spools. Two spools would be used: one would hold and dispense the untreated (bare) driveshaft, and the other would receive the treated driveshaft after the extrusion process. The driveshaft would be attached to both spools, and tension would be applied to the driveshaft by pulling the two spools apart. To begin the helical extrusion, the receiving spool would be simultaneously rotated and wound, with the direction of rotation being perpendicular to the direction of winding so as to twist the driveshaft and wind it onto the receiving spool. The dispensing spool would simultaneously unwind and rotate, thereby imparting an axial sliding motion and a circumferential twisting motion to the driveshaft as described above.

Figure 14:
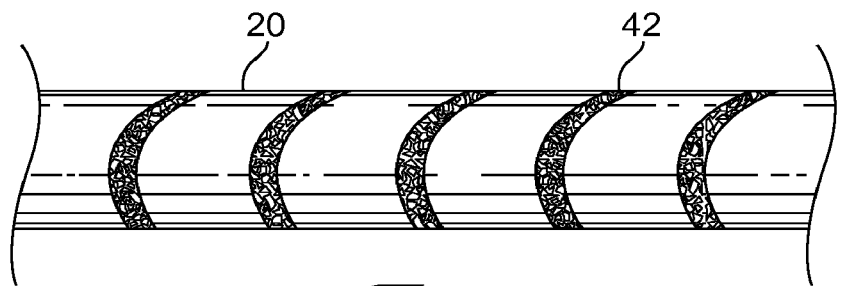
FIG. 14 is a partial plan view of a drive shaft having a surface portion roughened in a helical pattern.

A process of bonding or attaching a helical winding to the drive shaft with an enhanced mechanical lock can be described with respect to FIG. 14. In this process the outer surface of the drive shaft 20 is mechanically or chemically roughened in the pattern or path 42 of the helix wind by ablating, sand blasting or the like as shown in FIG. 14. A helix in the desired pattern is then formed from a wire by coiling it around the drive shaft over the roughened path. The coil is mechanically locked in place by the high level of friction with the roughened drive shaft surface. In some embodiments, welding or adhesives might be used to augment the frictional force holding the helix to the drive shaft. This process results in the production of a helical drive shaft comprising a drive shaft having a roughened surface patterned in the shape of a helix, and a helical winding overlying the drive shaft having a pitch which follows the roughened surface pattern. In an alternate embodiment, the entire drive shaft surface may be roughened to facilitate alignment and assembly. In this embodiment, the process results in the production of a helical drive shaft with a fully-roughened surface along all its length, and a helical winding overlying the drive shaft.

Figure 15:
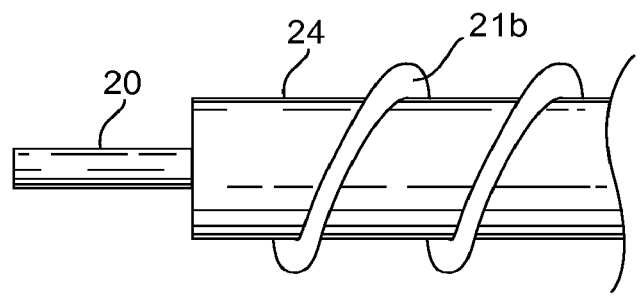
FIG. 15 is a partial plan view of a drive shaft having an auger blades formed in accordance with anther embodiment of the invention.
Figure 16:
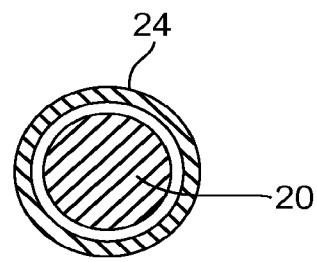
FIGS. 16 and 17 are cross-sectional views of the embodiment of FIG. 15 during different steps in the process of forming the auger blades.
Figure 17:
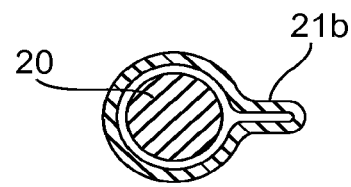

FIG. 15 shows a portion of a drive shaft 20 with auger blades 21b formed by another process. In this method the drive shaft 20 is placed into an extruded thermoplastic polymer tube 24 leaving a suitable gap between the drive shaft 20 and the tube 24. In one example, the tube inner diameter may be about 0.003" to 0.015" larger than the drive shaft outer diameter ($D_{DS}$) as shown in FIG. 16. One end of the tube 24 is attached to the drive shaft 20. Heat is applied focally to a section of the tube 24 immediately adjacent to the anchored region of the tube, and this heat is sufficient to soften the polymer tube, for example 400 to 800° F. FIG. 17 is a cross sectional view of a portion of the drive shaft 20 illustrating the process of forming an auger blade 21b. As the heated polymer tube is twisted, the softened polymer buckles in the heated region, as illustrated in FIG. 17. Eventually, the gap between the large polymer tube 24 and the drive shaft 20 will seal closed in that region. This eliminates the air gap that previously existed between the polymer tube 24 and the drive shaft 20, and it creates a fin structure on one side of the tube that, as it is twisted, will wrap up on itself creating a helix that functions as the blade 21b of an auger. As the polymer cools, it hardens and retains the helical shape. An auger 21b is thus formed and attached to the drive shaft 20 via a continuous process from the attached end of the tube to the opposite end. The wall thickness of the polymer tube 24 ($T_{POLY}$) will largely determine the fin thickness in the circumferential direction which will be about twice the wall thickness. The diameter of the original polymer tube ($D_{POLY}$) will, to a large extent, control the radial length of the fin (and thus, the outer diameter of the final helix). In this embodiment the radial length of the fold or auger blade will be approximately equal to: ($\pi D_{POLY} - \pi D_{DS}$)/2 and the diameter of the resulting auger will be approximately equal to: $D_{DS} + (\pi D_{POLY} - \pi D_{DS}) + 2T_{POLY}$. The pitch is controlled by the rate of twist as the polymer tube and drive shaft are pulled axially through the heat source.

Figure 18:
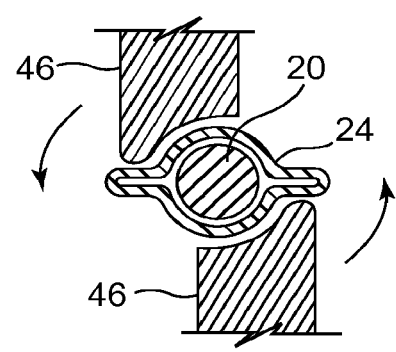
FIG. 18 is a cross-sectional view of a drive shaft having auger blades and forming tools used to form the auger blades according to another embodiment of the invention.

In an alternative embodiment, the heating and twisting operation is replaced by heating and sculpting. In this approach, the oversized thermoplastic polymer tubing is shaped by applying one or more heated tools 46 that spin around the drive shaft 20 and push against the polymer tube 24, simultaneously softening and sculpting it into a cross-section with fins, as shown in FIG. 18. In this embodiment, each tool creates an individual fin in the cross-section of the auger by folding the tube over upon itself and closing the air gap resulting from the large ID of the polymer tube. The resulting shape is a double helix or other multi-armed helix of polymer that is wrapped around a metal core driveshaft and serves as an auger. In yet another embodiment, a single heated tool is used to incompletely close the air gap by sculpting from one side only. In this approach, the heated tool spins around the driveshaft in a helical shape, and it creates one large fin of a desired size, for example, 0.002" to 0.012" in height. The single tool does not fully compress the oversized tubing onto the driveshaft, and a small bulge is left approximately 180 degrees away from the main fin. This bulge is relatively small, 0.0005" to 0.005" in length. In this embodiment, the result is a polymer double helix with one helical wind that is substantially larger than the other. The polymer double helix is wrapped around a metal driveshaft and serves as an auger.

In another method the helical winding is formed over the drive shaft by inserting the drive shaft into a polymer tube which is extruded in the shape of a star such as star shaped member 26 shown in FIG. 5. The tube thus has a cross-sectional shape having alternating peaks 27 and valleys 29. One end of the tube is attached to the cylindrical drive shaft. While applying heat to the tube at a temperature sufficient to soften the polymer tube, for example 425° F., the free end of the tube is twisted in a controlled manner. The tube is twisted such that the radially extending peaks 27 of the star form a helical winding having the desired pitch, which may be controlled by the rate of rotation as the device is twisted. The number of peaks 27 of the cross-sectional shape can be varied as desired to create an auger with a single blade or multiple blades.

In a similar method a helical winding is formed over the drive shaft with an extruded polymer tube having a star shaped cross-section such as star shaped member 26 shown in FIG. 5. In the method, however, the tube 26 is twisted during the extrusion process to form a polymer tube having helical windings. The polymer tube 26 is extruded with a spinning die or a spinning puller assembly to have a generally tube-shaped form, with an air-filled cylindrical space or lumen running down the center and a thin tube of polymer over which a helix is formed. The lumen is slightly larger than the drive shaft to allow the drive shaft to be inserted through the polymer tube. The polymer tube with preformed helical winding is attached to the drive shaft by means of adhesives, which may include UV-cured adhesives, IR-cured adhesives, or thermally-cured adhesives.

In another method a flat wire of copper, stainless steel, NiTi, a cobalt alloy, or other metal alloy having a rectangular cross-section is coiled in a helical configuration using a commercially available mechanical winder or coiler to form a helical winding having the desired configuration, similar to auger blade 21*a* shown in FIG. 6. The drive shaft is placed within the helical winding and a thick parylene coating or other polymer-based coating is applied over both, such as by a vapor deposition process. The parylene or other polymer coating functions to attach the helical winding or auger to the cylindrical portion and further provides the helix with a lubricious coating that reduces torque requirements and improves helix efficiency. This process results in the production of a helical drive shaft comprising a drive shaft, a helical winding and an outer coating or layer of parylene. The bond between drive shaft and helix may be strengthened by welding, gluing, soldering, or brazing the helix to the drive shaft in two or more locations prior to vapor deposition coating.

In another method the helical winding is attached to the drive shaft by laser welding a helically coiled flat wire, similar to auger blade 21*a* shown in FIG. 6, to the drive shaft. In this method the wire is coiled to form a helical winding or auger by using a mechanical winder or coiler to form a helix over a temporary mandrel, which is then removed. The wire is a metal such as copper, stainless steel, titanium, or equivalent or an alloy such as MP35N. After forming the helical winding it is then placed or slid over the drive shaft. The helical winding is then attached by welding it to the drive shaft. The weld may be a continuous weld, a series of spot welds, or a series of seam welds.

In a further method a drive shaft is combined with a helical winding using a brazing process. In this method a helical winding of metal wire such as auger blade 21*a* shown in FIG. 6 is coated along its entire surface to a thickness of 0.0005" to 0.005" with a braze material such as silver, gold, tin, copper, platinum, or a suitable alloy. The helical winding is placed over the drive shaft and the assembled unit is then fired in an oven at a suitable temperature, usually above about 800° F., to join the helical winding to the cylindrical portion. The combined unit includes the drive shaft, a layer of brazed metal, and the helically coiled wire.

In another method a helical winding of metal wire such as auger blade 21*a* shown in FIG. 6 is welded to the drive shaft by arc welding. In this method the helical winding is placed over the drive shaft, and a high voltage is applied between the helix and the drive shaft to arc weld the helix to the drive shaft. The drive shaft may be coated with an insulation material (such as glass, PTFE, or another polymer) to ensure that there is only contact between the drive shaft and helix where welding is desired. In an alternate embodiment of this method, a conductive layer or conductive nodules, for example of metal alloys with good conductivity, could be applied to the outer surface of the drive shaft to encourage arc formation at specific locations. In another embodiment, the arc welding could be performed while wire was being coiled directly onto the drive shaft. Voltage could be applied between the drive shaft and the helix at the location where the wire was being coiled onto the drive shaft with the intention of inducing an arc between the drive shaft and the helix at the moment that the wire first touches the drive shaft. The voltage could be applied either continuously or in bursts, and conductive nodules or insulating patches could be applied to minimize electrical conduction through sites other than the desired arc locations.

Another method of making a helical drive shaft involves the use of an electropolishing or a galvanic cell process. First, a metal shaft is produced of the material desired for the helix, such as stainless steel, NiTi, a cobalt alloy, or zinc. The metal shaft is masked to leave exposed only those areas defining the pattern of the helical winding by covering it tightly with a helix-shaped shell. Then the drive shaft is charged in an acid bath or a metal-salt bath to remove the metal over the unmasked areas. The masked areas are protected by the helix-shaped shell covering them, so material is removed preferentially from the unmasked regions. When the desired thickness is removed, the helix is removed from the bath, and the mask is removed from the helix.

In another method the helical winding is swaged to the drive shaft. In this method a helical winding such as auger blade 21*a* shown in FIG. 6 is formed with an inner diameter just large enough to allow the drive shaft to be inserted with a tight fit. The combined drive shaft and helical winding are then placed through a mechanical compression system that provides radial force from multiple sides of the helix simultaneously to permanently and plastically deform the helix and reduce its inner diameter. The result is a mechanical lock that holds the helix on the drive shaft. In an alternate embodiment, the strength of this bond may be supplemented by welding the helix onto the driveshaft in two or more locations after swaging.

In another method the helical drive shaft is made using a vacuum forming process. In this method a drive shaft such as drive shaft 20*a* shown in FIG. 3 is placed within a helical winding such as auger blade 21*a* shown in FIG. 6. A tubular plastic, such as one having a wall thickness of 0.00025" to 0.003", is then placed over the combined unit and connected on both ends to a vacuum system. A vacuum is then applied to the interior of the tubular structure to cause it to compress and stretch over the exterior surface of the combined drive shaft and helical winding locking them together. The result of this process produces an outer layer or coating comprised of the plastic material which permanently attaches the helical winding to the drive shaft. Optionally, the process may be performed inside an environment where heat is applied (e.g., an oven, or a hot fluidized bed), and the heat would soften the polymer and allow the ends of the tube to seal upon the drive shaft. This would assist in excluding air from the inside of the polymer tube. Another optional embodiment would expose the outer surface of the polymer tube to high pressures instead of or in addition to applying a vacuum on the inside of the tube. In this way, the tube could be deflated more fully and form a more effective crimp upon the helix, because a higher pressure differential could be attained across the tube.

In a further method a helical winding, such as auger blade 21*a* shown in FIG. 6, is formed of a bimetal. The bimetal may comprise a first metal, such as a strong metal with high melting point, including for instance stainless steel, NiTi, or a cobalt alloy. The second metal may be a solder-like or brazing material, such as silver, gold, tin, copper, or platinum. This brazing or soldering material forms a thin coating of thickness 0.0005" to 0.005" on one or more edges of the wire cross-section. Bimetal wire may be dual-extruded using the bimetal material, or in an alternate embodiment, a wire may be extruded of the stainless steel, NiTi, or cobalt alloy and then coated with the brazing or soldering material after extrusion. In both these embodiments, the bimetal is formed into a wire before being wound into a helix. The drive shaft is then placed within the bimetal helical winding and heated in an oven to a temperature sufficient to melt the solder like material and solder the helical winding to the drive shaft.

In another method a helical drive shaft is formed using a helical winding, such as auger blade 21a shown in FIG. 6, and a drive shaft that has been coated with a thermoplastic polymer having a low glass transition temperature such as a nylon, laminated over the drive shaft in a thickness which in one embodiment ranges from 0.0005" to 0.005" and in another embodiment ranges from 0.0015" to 0.0035". The coated drive shaft, such as drive shaft 20a shown in FIG. 3, is inserted into the helical winding with a diametric gap of up to 0.005" separating them. In one embodiment the separation is up to 0.003". The combined unit is then placed in an oven and heated to a temperature which, in one embodiment, is in the range of 100° C. to 300° C. and in another embodiment is in the range 180° C. to 200° C. The temperature is selected to be sufficient to soften the polymer into the helix. Wicking preferentially keeps the polymer at the interface between the helix and the drive shaft and causes the polymer to form a slight meniscus onto the helix. When cooled, this meniscus hardens and mechanically anchors the helix in place. In another embodiment, additional strength is provided by welding the helix to the drive shaft in one or more locations, either by using a laser to ablate sections of the laminate before welding or by designating specific weld locations on the drive shaft that are left without laminate. The polymer may be reflowed to form the meniscus around the helix either before or after this welding is performed.

In another method a helical drive shaft is formed using an uncoated drive shaft and a helical winding, such as auger blade 21a shown in FIG. 6, that has been coated with a polymer having a low melting temperature. An example of this polymer is a nylon or another thermoplastic polymer that is capable of being reflowed, and the chosen polymer might be applied to the helix in a thickness which in one embodiment ranges from 0.0005" to 0.005" and in another embodiment ranges from 0.0015" to 0.0035" by dip-coating or spray-coating or another method. The drive shaft, such as drive shaft 20a shown in FIG. 3, is inserted into the coated helical winding. The combined unit is then placed in an oven and heated to a temperature in the range of 100° C. to 300° C. in a first embodiment and in another embodiment is in the range 180° C. to 200° C. The temperature is selected to be sufficient to melt the polymer into the drive shaft. Wicking preferentially keeps the polymer at the interface between the helix and the drive shaft and causes the polymer to form a slight meniscus onto the helix. When cooled, this meniscus mechanically anchors the helix in place. In another embodiment, additional strength is provided by welding the helix to the driveshaft in one or more locations, either by using a laser to ablate sections of the laminate before welding or by designating specific weld locations on the helix which are left without laminate.

In another method a drive shaft, such as drive shaft 20a shown in FIG. 3, is placed in a tube that is filled with an adhesive that is designed to be cured by exposure to ultraviolet light. The tube surrounding the drive shaft has a diameter that is equivalent to the desired diameter of the desired helical winding. The tube is masked with a pattern in the shape of the desired helix, and this masking is designed to block light in the ultraviolet range, for example, by using UV-opaque paint to cover the tube with a helix pattern. The tube is then irradiated in UV light to harden the UV adhesive in the unmasked portions of the tube. In the portions of the tube that are masked, the masking prevents ultraviolet light from curing the adhesive, so the adhesive remains soft. Next, the tube is rinsed in an acetone bath to remove the unhardened portions of UV adhesive underlying the masked portions of the tube.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments. The invention is intended to comprise, at least, the following.

A method of making a helical drive shaft having a helical auger blade with a desired pitch, depth, width and outer diameter comprising: coating a cylindrical drive shaft with a layer of polymer to a thickness greater than the outer diameter of the auger blade; and rotating the coated drive shaft through a die having threads configured to form the auger blade in the polymer with the desired pitch, depth, width and outer diameter.

A method of making a helical drive shaft having a helical auger blade with a desired pitch, depth, width and outer diameter comprising: coating a cylindrical drive shaft with a layer of polymer to a thickness conforming to the outer diameter of the auger blade; and cutting a helical groove in the polymer to form the auger blade in the polymer with the desired pitch, depth, width and outer diameter.

A method of making a helical drive shaft having a helical auger blade with a desired pitch, depth, width and outer diameter comprising: dripping glass onto the outer surface of a cylindrical drive shaft in a helical pattern; shaping the glass on the surface of the drive shaft into a desired base shape; and after the glass has been shaped coating the surface of the drive shaft with a polymer to form a helical auger blade having the desired pitch, depth, width and outer diameter of the auger blade in a helical pattern overlying the shaped glass.

A method of making a helical drive shaft having a helical auger blade with a desired pitch, depth, width and outer diameter comprising: extruding polymer through a die in a desired shape of the auger blade; and while it is pliable, winding the extruded polymer onto the outer surface of a cylindrical drive shaft in a helical pattern, the polymer forming a helical auger blade with the desired pitch, depth, width and outer diameter.

A method of making a helical drive shaft having a helical auger blade with a desired pitch, depth, width and outer diameter comprising: roughening the surface of a cylindrical drive shaft; and placing a wire helix over the cylindrical drive shaft, the helix having an inner surface which overlies the roughened surface of the drive shaft, the roughened surface creating a frictional attachment between the drive shaft and the wire helix.

A method of making a helical drive shaft having a helical auger blade with a desired pitch, depth, width and outer diameter comprising: placing a cylindrical drive shaft into an extruded polymer tube, the polymer tube having a circular cross-section; attaching one end of the polymer tube to the drive shaft; applying heat to the tube overlying the drive shaft at a temperature sufficient to soften the polymer tube; and twisting the softened polymer tube causing a portion of the tube to buckle, the buckled portion of the tube forming a helical auger blade with a desired pitch, depth, width and outer diameter.

A method of making a helical drive shaft having a helical auger blade with a desired pitch, depth, width and outer diameter comprising: placing a cylindrical drive shaft into an extruded polymer tube, the polymer tube having a star shaped cross-section defined by the intersection of the tube with a plane which is perpendicular to a longitudinal axis of the tube, the star shaped cross-section defining alternating peaks and valleys; attaching one end of the polymer tube to the drive shaft; applying heat to the tube overlying the drive shaft at a temperature sufficient to soften the polymer tube; and twisting the heated polymer tube such that each peak of the tube forms a helical auger blade with the desired pitch, depth, width and outer diameter.

A method of making a helical drive shaft having a helical auger blade with a desired pitch, depth, width and outer diameter comprising: extruding a polymer tube through a die shaped to provide the tube with a star shaped cross-section defined by the intersection of the tube with a plane which is perpendicular to a longitudinal axis of the tube, the star shaped cross-section defining alternating peaks and valleys; twisting the polymer tube as it is extruded such that each peak of the polymer tube forms a helical auger blade with the desired pitch, width, and outer diameter; and placing a cylindrical drive shaft into the extruded polymer tube.

A method of making a helical drive shaft having a helical auger blade with a desired pitch, depth, width and outer diameter comprising: forming a flat metal wire into a helical coil, the helical coil having an inner diameter and an outer diameter; placing a cylindrical drive shaft within the inner diameter of the helical coil; and after the drive shaft is placed within the helical coil applying a coating of parylene or other polymer over the drive shaft and helical coil to attach the helical coil to the drive shaft.

A method of making a helical drive shaft having a helical auger blade with a desired pitch, depth, width and outer diameter comprising: forming a flat metal wire into a helical coil, the helical coil having an inner diameter and an outer diameter; placing a cylindrical drive shaft within the inner diameter of the helical coil; and welding the helical coil to the drive shaft by one of continuous welding, spot welding, or seam welding, the helical coil forming an auger blade having the desired pitch, depth, width and outer diameter.

A method of making a helical drive shaft having a helical auger blade with a desired pitch, depth, width and outer diameter comprising: forming a flat metal wire into a helical coil, the helical coil having an inner surface defining an inner diameter and an outer surface defining an outer diameter; coating the surface of the helical coil with a braze material; placing a cylindrical drive shaft within the inner diameter of the helical coil; and after the drive shaft is placed within the inner diameter of the helical coil, applying heat at a temperature sufficient to melt the braze material and join the helical coil to the drive shaft, the helical coil forming an auger blade having the desired pitch, depth, width and outer diameter.

A method of making a helical drive shaft having a helical auger blade with a desired pitch, depth, width and outer diameter comprising: forming a flat metal wire into a helical coil, the helical coil having an inner surface defining an inner diameter and an outer surface defining an outer diameter, the inner surface being coated with a conductive layer of welding material; placing a cylindrical drive shaft within the inner diameter of the helical coil; and applying a high voltage between the helical coil and the drive shaft to weld the inner surface of the helical coil to an outer surface of the drive shaft.

A method of making a helical drive shaft having a helical auger blade with a desired pitch, depth, width and outer diameter comprising: masking a cylindrical drive shaft to leave exposed only areas defining the pattern of a helical winding; placing the masked drive shaft in an acid or metal-salt bath to remove metal over unmasked areas of the drive shaft; and when a desired thickness of metal has been removed, removing the drive shaft from the bath.

A method of making a helical drive shaft having a helical auger blade with a desired pitch, depth, width and outer diameter comprising: forming a flat metal wire into a helical coil, the helical coil having an inner surface defining an inner diameter and an outer surface defining an outer diameter, the inner surface being coated with a conductive layer of welding material; placing a cylindrical drive shaft within the inner diameter of the helical coil; and after the drive shaft is placed within the inner diameter of the helical coil, locking the helical coil to the drive shaft by placing the drive shaft and inner coil through a mechanical compression device that provides radial force from multiple sides of the helical coil simultaneously to permanently and plastically deform the helical coil and reduce its inner diameter.

A method of making a helical drive shaft having a helical auger blade with a desired pitch, depth, width and outer diameter comprising: placing a cylindrical drive shaft within a helical winding; placing the combined drive shaft and winding within the lumen or interior of a plastic tube; connecting the interior of the tube to a source of vacuum; and applying a vacuum to the interior of the plastic tube to compress and stretch the tube over an exterior surface of the combined drive shaft and helical winding to attach the winding to the drive shaft.

A method of making a helical drive shaft having a helical auger blade with a desired pitch, depth, width and outer diameter comprising: forming a bimetal wire into a helical coil, the bimetal comprising a metal having a high melting point and a metal having a low melting point, the helical coil having an inner surface defining an inner diameter and an outer surface defining an outer diameter; placing a cylindrical drive shaft within the inner diameter of the helical coil; and after the drive shaft is placed within the inner diameter of the helical coil, applying heat at a temperature sufficient to melt the metal having a low melting point and join the helical coil to the drive shaft, the helical coil forming an auger blade having the desired pitch, depth, width and outer diameter.

A method of making a helical drive shaft having a helical auger blade with a desired pitch, depth, width and outer diameter comprising: coating a cylindrical drive shaft with a polymer; placing the cylindrical drive shaft within a helical winding; and after the drive shaft is placed within the helical winding, applying heat at a temperature sufficient to melt the polymer coating and join the helical winding to the drive shaft, the helical coil forming an auger blade having the desired pitch, depth, width and outer diameter.

A method of making a helical drive shaft having a helical auger blade with a desired pitch, depth, width and outer diameter comprising: coating a helical winding with a polymer; placing a cylindrical drive shaft within the helical winding; and after the drive shaft is placed within the helical winding, applying heat at a temperature sufficient to melt the polymer coating and join the helical winding to the drive shaft, the helical coil forming an auger blade having the desired pitch, depth, width and outer diameter.

A method of making a helical drive shaft having a helical auger blade with a desired pitch, depth, width and outer diameter comprising: placing a cylindrical drive shaft within an adhesive filled tube; masking the tube with a masking agent selected to block light in the ultraviolet range to leave exposed only areas defining the pattern of a helical winding; irradiating the masked tube in ultraviolet light to harden the adhesive in unmasked portions of the tube; rinsing the tube in a solvent bath to remove unhardened portions of the adhesive, remaining hardened portions of the adhesive forming an auger blade having the desired pitch, depth, width and outer diameter.

A helical drive shaft having a helical auger blade with a desired pitch, depth, width and outer diameter comprising: a metal wire having a rectangular cross-section wound to form a helical coil having an inner surface defining an inner diameter and an outer surface defining an outer diameter, and a cylindrical drive shaft positioned within the inner diameter of the helical coil, the drive shaft having an outer surface attached to the inner surface of the helical coil, the helical coil being shaped to form a helical auger blade having the desired pitch, depth, width and outer diameter.

A helical drive shaft having a helical auger blade with a desired pitch, depth, width and outer diameter comprising: a polymer tube having an inner surface defining an inner diameter and an outer surface defining an outer diameter, the outer surface being shaped to form a fin extending radially from the polymer tube in a helical pattern; and a cylindrical drive shaft positioned within the inner diameter of the polymer tube, the drive shaft having an outer surface attached to the inner surface of the polymer tube, the helical fin being shaped to form a helical auger blade having the desired pitch, depth, width and outer diameter.

A helical drive shaft having a helical auger blade with a desired pitch, depth, width and outer diameter comprising: a cylindrical drive shaft having an outer surface; a glass fin extending radially from the outer surface of the cylindrical drive shaft in a helical pattern; and an outer coating or layer of polymer over the drive shaft and fin, the glass fin being shaped to form a helical auger blade having the desired pitch, depth, width and outer diameter.

A helical drive shaft having a helical auger blade with a desired pitch, depth, width and outer diameter comprising: a cylindrical drive shaft having an outer surface; and an extruded polymer portion having an inner surface and an outer surface, the polymer portion being wound about the cylindrical drive shaft such that the inner surface of the polymer portion is attached to the outer surface of the cylindrical drive shaft, the polymer portion extending radially from the outer surface of the cylindrical drive shaft in a helical pattern to form a helical auger blade having the desired pitch, depth, width and outer diameter.

A material removal device comprising: a tubular sheath having proximal and distal ends and a lumen; a helical drive shaft extending through the lumen of the tubular sheath, the helical drive shaft including a helical winding portion and a cylindrical portion, the cylindrical portion positioned within an inner diameter of the helical winding portion and being attached to the winding portion by one of the methods described above, the helical winding forming an auger blade having a desired pitch, depth, width, and outer diameter; and a cutting element attached at a distal portion of the helical drive shaft.

A material removal device comprising: a tubular sheath having proximal and distal ends and a lumen; a helical drive shaft according to one of as described herein extending through the lumen of the tubular sheath, the helical drive shaft including a helical winding portion forming an auger blade having a desired pitch, depth, width, and outer diameter; and a cutting element attached at a distal portion of the helical drive shaft.

What is claimed is:

1. A method of making a helical drive shaft having a helical auger blade with a desired pitch, depth, width and outer diameter comprising:
   coating a cylindrical drive shaft with a polymer;
   after said coating a cylindrical drive shaft with a polymer, placing the cylindrical drive shaft within a helical winding; and
   after the drive shaft is placed within the helical winding, applying heat at a temperature sufficient to melt the polymer coating and join the helical winding to the drive shaft, the helical coil forming an auger blade having the desired pitch, depth, width and outer diameter.

2. The method of claim 1 wherein the helical winding comprises a metal wire made of copper, stainless steel, NiTi, a cobalt alloy, or other metal alloy having a rectangular cross-section with desired dimensions.

3. The method of claim 1 wherein the polymer comprises a thermoplastic polymer having a low glass transition temperature.

4. The method of claim 3 wherein the thermoplastic polymer is nylon.

5. The method of claim 1 wherein the polymer coating has a thickness in the range of 0.0005" to 0.005".

6. The method of claim 1 wherein heat is applied at a temperature in the range of 100° C. to 300° C.

7. The method of claim 1 wherein the drive shaft comprises wire wound in alternating right and left hand layers.

8. The method of claim 1, further comprising forming a meniscus of the polymer on the helical winding during said applying heat.

9. The method of claim 8, further comprising cooling the polymer after said applying heat, wherein during cooling the meniscus hardens and mechanically anchors to the helical winding.

10. The method of claim 9, further comprising spot welding the helical winding to the cylindrical drive shaft at a plurality of locations.

11. A method of making a helical drive shaft having a helical auger blade with a desired pitch, depth, width and outer diameter comprising:
    coating a helical winding with a polymer;
    after said coating a helical winding with a polymer, placing a cylindrical drive shaft within the helical winding; and
    after the drive shaft is placed within the helical winding, applying heat at a temperature sufficient to melt the polymer coating and join the helical winding to the drive shaft, the helical coil forming an auger blade having the desired pitch, depth, width and outer diameter.

12. The method of claim 11 wherein the helical winding comprises a metal wire made of copper, stainless steel, NiTi, a cobalt alloy, or other metal alloy having a rectangular cross-section with desired dimensions.

13. The method of claim 11 wherein the polymer comprises a thermoplastic polymer having a low glass transition temperature.

14. The method of claim 13 wherein the thermoplastic polymer is nylon.

15. The method of claim 11 wherein the polymer coating has a thickness in the range of 0.0005" to 0.005".

16. The method of claim 11 wherein heat is applied at a temperature in the range of 100° C. to 300° C.

17. The method of claim 11 wherein the drive shaft comprises wire wound in alternating right and left hand layers.

18. The method of claim 11, further comprising forming a meniscus of the polymer on the helical winding during said applying heat.

19. The method of claim 18, further comprising cooling the polymer after said applying heat, wherein during cooling the meniscus hardens and mechanically anchors to the helical winding.

20. The method of claim 19, further comprising spot welding the helical winding to the cylindrical drive shaft at a plurality of locations.

* * * * *